United States Patent
Naydo et al.

(10) Patent No.: US 8,783,305 B2
(45) Date of Patent: *Jul. 22, 2014

(54) POWDER FILLING APPARATUS AND METHODS FOR THEIR USE

(75) Inventors: Kyle A Naydo, Mountain View, CA (US); Derrick J Parks, Belmont, CA (US); Patrick Reich, San Jose, CA (US); Gordon Stout, El Cerrito, CA (US); Xuyen Pham, Fremont, CA (US); Michael J Rocchio, Hayward, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/301,414

(22) Filed: Nov. 21, 2011

(65) Prior Publication Data

US 2012/0152975 A1    Jun. 21, 2012

Related U.S. Application Data

(66) Continuation of application No. 10/360,603, filed on Feb. 6, 2003, now Pat. No. Re. 42,942, which is an application for the reissue of Pat. No. 6,182,712, Substitute for application No. 08/949,047, filed on Oct. 10, 1997.

(60) Provisional application No. 60/100,437, filed on Oct. 10, 1997.

(51) Int. Cl.
*B65B 1/08* (2006.01)

(52) U.S. Cl.
USPC ............... 141/67; 141/18; 141/125; 141/129; 141/234; 141/237; 141/238; 141/241; 141/242; 141/280; 141/286

(58) Field of Classification Search
USPC ............... 141/2–8, 12, 18, 67–71, 83, 94, 95, 141/115, 125, 234, 237, 238, 241, 242, 141/286; 222/345, 346, 368, 189.06; 209/311, 312, 315, 318, 380, 344
See application file for complete search history.

(56) References Cited

U.S. PATENT DOCUMENTS 2,049,870 A    8/1936  Schiff
2,531,245 A    11/1950 Bailey
(Continued)

FOREIGN PATENT DOCUMENTS

CA    949786    6/1974
DE    531329    8/1931
(Continued)

OTHER PUBLICATIONS

Hungarian Search Report dated Feb. 25, 2000, corresponding to Hungarian Application No. P9902761.

(Continued)

*Primary Examiner* — Tuan N Nguyen
(74) *Attorney, Agent, or Firm* — Janah & Associates, PC

(57) ABSTRACT

The invention provides methods, systems and apparatus for the metered transport of fine powders into receptacles. According to one exemplary embodiment, an apparatus is provided which comprises a hopper having an opening. The hopper is adapted to receive a bed of fine powder. At least one chamber, which is moveable to allow the chamber to be placed in close proximity to the opening, is also provided. An element having a proximal end and a distal end is positioned within the hopper such that the distal end is near the opening. A vibrator motor is provided to vibrate the element when within the fine powder.

10 Claims, 14 Drawing Sheets

(56) References Cited

U.S. PATENT DOCUMENTS

| | | | |
|---|---|---|---|
| 2,540,059 A | 1/1951 | Stirn et al. | |
| 3,166,383 A | 1/1965 | Morris | |
| 3,254,766 A | 6/1966 | Anderson | |
| 3,446,404 A | 5/1969 | Mehta | |
| 3,578,778 A | 5/1971 | Matthews et al. | |
| 3,804,245 A | 4/1974 | Pendleton | |
| 3,871,626 A | 3/1975 | Wohlfarth | |
| 3,874,431 A | 4/1975 | Aronson | |
| 3,895,111 A | 7/1975 | Corey et al. | |
| 3,899,417 A | 8/1975 | Morris | |
| 4,005,668 A | 2/1977 | Washington et al. | |
| 4,067,225 A | 1/1978 | Dorman | |
| 4,106,535 A | 8/1978 | Davis | |
| 4,320,657 A | 3/1982 | Johnson, III | |
| 4,371,101 A | 2/1983 | Cane et al. | |
| 4,481,987 A | 11/1984 | Burns | |
| 4,509,568 A | 4/1985 | Kawaguchi | |
| 4,616,152 A | 10/1986 | Saito et al. | |
| 4,640,322 A | 2/1987 | Ballester | |
| 4,684,041 A | 8/1987 | Jones et al. | |
| 4,688,610 A | 8/1987 | Campbell | |
| 4,709,837 A | 12/1987 | Erdman | |
| 4,719,409 A | 1/1988 | Dorman | |
| 4,864,876 A | 9/1989 | Botzolakis et al. | |
| 4,953,643 A | 9/1990 | Ellion et al. | |
| 4,974,646 A | 12/1990 | Martin et al. | |
| 4,984,128 A | 1/1991 | Cebon | |
| 5,140,756 A | 8/1992 | Iwaya et al. | |
| 5,143,126 A * | 9/1992 | Boesch et al. | 141/1 |
| 5,219,008 A | 6/1993 | Shannon | |
| 5,287,897 A | 2/1994 | Gamberini | |
| 5,366,122 A | 11/1994 | Guentert | |
| 5,377,727 A | 1/1995 | Ueda et al. | |
| 5,456,298 A | 10/1995 | Tennis | |
| 5,544,683 A | 8/1996 | Guhl | |
| 5,575,280 A | 11/1996 | Gupte et al. | |
| 5,753,302 A | 5/1998 | Sun et al. | |
| 5,765,607 A | 6/1998 | Ansaloni | |
| 5,826,633 A * | 10/1998 | Parks et al. | 141/18 |
| 5,858,099 A | 1/1999 | Sun et al. | |
| 5,865,012 A | 2/1999 | Hansson et al. | |
| 5,875,824 A | 3/1999 | Atwell et al. | |
| 6,045,753 A | 4/2000 | Loewy et al. | |
| 6,063,194 A | 5/2000 | Poliniak et al. | |
| 6,065,509 A | 5/2000 | Bonney et al. | |
| 6,096,368 A | 8/2000 | Sun | |
| 6,168,666 B1 | 1/2001 | Sun | |
| 6,182,712 B1 | 2/2001 | Stout et al. | |
| 6,267,155 B1 | 7/2001 | Parks et al. | |
| 6,294,024 B1 | 9/2001 | Sun et al. | |
| 6,440,486 B2 | 8/2002 | Sun et al. | |
| 6,471,096 B1 | 10/2002 | Dave | |
| 6,684,917 B2 | 2/2004 | Zhu et al. | |
| 6,764,695 B1 | 7/2004 | Watanabe et al. | |
| 6,776,361 B1 | 8/2004 | Watanabe et al. | |
| 7,237,699 B2 | 7/2007 | Zill et al. | |
| RE42,942 E * | 11/2011 | Stout et al. | 141/67 |
| 2002/0056206 A1 | 5/2002 | Pace et al. | |
| 2002/0076382 A1 | 6/2002 | Kaplan et al. | |

FOREIGN PATENT DOCUMENTS

| | | |
|---|---|---|
| DE | 3210787 | 10/1983 |
| DE | 234397 | 4/1986 |
| DE | 3607187 | 9/1987 |
| EP | 0432126 | 6/1991 |
| EP | 0839783 | 6/1998 |
| FR | 2537545 | 6/1984 |
| GB | 703745 | 2/1954 |
| GB | 961989 | 6/1964 |
| GB | 1109407 | 4/1968 |
| GB | 1420364 | 1/1976 |
| GB | 1475593 | 6/1977 |
| GB | 2167387 | 5/1986 |
| GB | 1309424 | 3/1993 |
| GB | 9515340.9 | 7/1995 |
| HU | 179529 | 2/1982 |
| HU | 186531 | 6/1984 |
| HU | 189881 | 5/1988 |
| JP | 58-144922 | 4/1985 |
| JP | 02-19201 | 1/1990 |
| SU | 949786 | 6/1974 |
| SU | 1061030 | 12/1983 |
| WO | WO9509615 | 4/1995 |
| WO | WO9509616 | 4/1995 |
| WO | WO9521798 | 8/1995 |
| WO | WO9604082 | 2/1996 |
| WO | WO9608284 | 3/1996 |
| WO | WO9705018 | 2/1997 |
| WO | WO9741031 | 11/1997 |
| WO | WO99/19215 | 4/1999 |
| WO | WO01/76205 | 10/2001 |

OTHER PUBLICATIONS

International Search Report mailed Jul. 28, 1997, corresponding to International Application No. PCT/US97/04994.

Japanese Office Action mailed Jul. 4, 2006, corresponding to Japanese Patent Application No. 9-538880.

Supplementary European Search Report completed Sep. 11, 2001, corresponding to European Application No. EP 97917652.

Written Opinion mailed Jun. 26, 1998, corresponding to International Application No. PCT/US97/04994.

* cited by examiner

POWDER FILLING APPARATUS AND METHODS FOR THEIR USE

CROSS REFERENCE TO RELATED APPLICATIONS

This application is a continuation of U.S. patent application Ser. No. 10/360,603, filed Feb. 6, 2003 (U.S. Pat. No. RE42,942), which is a reissued patent of U.S. Pat. No. 6,182,712, issued Feb. 6, 2001, which is a continuation-in-part application of and claims the benefit of U.S. Provisional Patent Application Ser. No. 60/100,437, which was converted from U.S. patent application Ser. No. 08/949,047, filed Oct. 10, 1997, the complete disclosures of which are herein incorporated by reference.

BACKGROUND OF THE INVENTION

1. Field of the Invention

The present invention relates generally to the field of fine powder processing, and particularly to the metered transport of fine powders. More particularly, the present invention relates to systems, apparatus and methods for filling receptacles with unit dosages of non-flowable but dispersible fine powdered medicaments, particularly for subsequent inhalation by a patient.

Effective delivery to a patient is a critical aspect of any successful drug therapy. Various routes of delivery exist, and each has its own advantages and disadvantages. Oral drug delivery of tablets, capsules, elixirs, and the like, is perhaps the most convenient method, but many drugs have disagreeable flavors, and the size of the tablets makes them difficult to swallow. Moreover, such medicaments are often degraded in the digestive tract before they can be absorbed. Such degradation is a particular problem with modern protein drugs which are rapidly degraded by proteolytic enzymes in the digestive tract. Subcutaneous injection is frequently an effective route for systemic drug delivery, including the delivery of proteins, but has a low patient acceptance and produces sharp waste items, e.g. needles, which are difficult to dispose. Since the need to inject drugs on a frequent schedule such as insulin one or more times a day, can be a source of poor patient compliance, a variety of alternative routes of administration have been developed, including transdermal, intranasal, intrarectal, intravaginal, and pulmonary delivery.

Of particular interest to the present invention are pulmonary drug delivery procedures which rely on inhalation of a drug dispersion or aerosol by the patient so that the active drug within the dispersion can reach the distal (alveolar) regions of the lung. It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery can be effective both for systemic delivery and for localized delivery to treat diseases of the lungs.

Pulmonary drug delivery (including both systemic and local) can itself be achieved by different approaches, including liquid nebulizers, metered dose inhalers (MDI's) and dry powder dispersion devices. Dry powder dispersion devices are particularly promising for delivering protein and polypeptide drugs which may be readily formulated as dry powders. Many otherwise labile proteins and polypeptides may be stably stored as lyophilized or spray-dried powders by themselves or in combination with suitable powder carriers. A further advantage is that dry powders have a much higher concentration than medicaments in liquid form.

The ability to deliver proteins and polypeptides as dry powders, however, is problematic in certain respects. The dosage of many protein and polypeptide drugs is often critical so it is necessary that any dry powder delivery system be able to accurately, precisely and repeatably deliver the intended amount of drug. Moreover, many proteins and polypeptides are quite expensive, typically being many times more costly than conventional drugs on a per-dose basis. Thus, the ability to efficiently deliver the dry powders to the target region of the lung with a minimal loss of drug is critical.

For some applications, fine powder medicaments are supplied to dry powder dispersion devices in small unit dose receptacles, often having a puncturable lid or other access surface (commonly referred to as blister packs). For example, the dispersion devices described in U.S. Pat. Nos. 5,785,049 and 5,740,794, the disclosures of which are herein incorporated by reference, are constructed to receive such a receptacle. Upon placement of the receptacle in the device, a multi-flow ejector assembly having a feed tube is penetrated through the lid of the receptacle to provide access to the powdered medicament therein. The multi-flow ejector assembly also creates vent holes in the lid to allow the flow of air through the receptacle to entrain and evacuate the medicament. Driving this process is a high velocity air stream which is flowed past a portion of the tube, such as an outlet end, to draw powder from the receptacle, through the tube, and into the flowing air stream to form an aerosol for inhalation by the patient. The high velocity air stream transports the powder from the receptacle in a partially de-agglomerated form, and the final complete de-agglomeration takes place in the mixing volume just downstream of the high velocity air inlets.

Of particular interest to the present invention are the physical characteristics of poorly flowing powders. Poorly flowing powders are those powders having physical characteristics, such as flowability, which are dominated by cohesive forces between the individual units or particles (hereinafter "individual particles") which constitute the powder. In such cases, the powder does not flow well because the individual particles cannot easily move independently with respect to each other, but instead move as clumps of many particles. When such powders are subjected to low forces, the powders will tend not to flow at all. However, as the forces acting upon the powder are increased to exceed the forces of cohesion, the powder will move in large agglomerated "chunks" of the individual particles. When the powder comes to rest, the large agglomerations remain, resulting in a non-uniform powder density due to voids and low density areas between the large agglomerations and areas of local compression.

This type of behavior tends to increase as the size of the individual particles becomes smaller. This is most likely because, as the particles become smaller, the cohesive forces, such as Van Der Waals, electrostatic, friction, and other forces, become large with respect to the gravitational and inertial forces which may be applied to the individual particles due to their small mass. This is relevant to the present invention since gravity and inertial forces produced by acceleration, as well as other effected motivators, are commonly used to process, move and meter powders.

For example, when metering the fine powders prior to placement in the unit dose receptacle, the powders often agglomerates inconsistently, creating voids and excessive density variation, thereby reducing the accuracy of the volumetric metering processes which are commonly used to meter in high throughput production. Such inconsistent agglomeration is further undesirable in that the powder agglomerates need to be broken down to the individual particles, i.e. made to be dispersible, for pulmonary delivery. Such de-agglomeration often occurs in dispersion devices by shear forces created by the air stream used to extract the medicament from the unit dose receptacle or other containment, or by other mechanical energy transfer mechanisms (e.g., ultrasonic, fan/impeller, and the like). However, if the small powder agglomerates are too compacted, the shear forces provided by the air stream or other dispersing mechanisms will be insufficient to effectively disperse the medicament to the individual particles.

Some attempts to prevent agglomeration of the individual particles are to create blends of multi-phase powders (typically a carrier or diluent) where larger particles (sometimes of multiple size ranges), e.g. approximately 50 µm, are combined with smaller drug particles, e.g. 1 µm to 5 µm. In this case, the smaller particles attach to the larger particles so that under processing and filling the powder will have the characteristics of a 50 μm powder. Such a powder is able to more easily flow and meter. One disadvantage of such a powder, however, is that removal of the smaller particles from the larger particles is difficult, and the resulting powder formulation is made up largely of the bulky flowing agent component which can end up in the device, or the patient's throat.

Current methods for filling unit dose receptacles with powdered medicaments include a direct pouring method where a granular powder is directly poured via gravity (sometimes in combination with stirring or "bulk" agitation) into a metering chamber. When the chamber is filled to the desired level, the medicament is then expelled from the chamber and into the receptacle. In such a direct pouring process, variations in density can occur in the metering chamber, thereby reducing the effectiveness of the metering chamber in accurately measuring a unit dose amount of the medicament. Moreover, the powder is in a granular state which can be undesirable for many applications.

Some attempts have been made to minimize density variations by compacting the powder within, or prior to depositing it in the metering chamber. However, such compaction is undesirable, especially for powders made up of only fine particles, in that it decreases the dispersibility of the powder, i.e. reduces the chance for the compacted powder to be broken down to the individual particles during pulmonary delivery with a dispersion device.

It would therefore be desirable to provide systems and methods for the processing of fine powders which would overcome or greatly reduce these and other problems. Such systems and methods should allow for accurate and precise metering of the fine powder when divided into unit doses for placement in unit dose receptacles, particularly for low mass fills. The systems and methods should further ensure that the fine powder remains sufficiently dispersible during processing so that the fine powder may be used with existing inhalation devices which require the powder to be broken down to the individual particles before pulmonary delivery. Further, the systems and methods should provide for the rapid processing of the fine powders so that large numbers of unit dose receptacles can rapidly be filled with unit dosages of fine powder medicaments in order to reduce cost.

2. Description of the Background Art

U.S. Pat. No. 5,765,607 describes a machine to meter products into containers and includes a metering unit to supply the product into containers.

U.S. Pat. No. 4,640,322 describes a machine which applies sub-atmospheric pressure through a filter to pull material directly from a hopper and laterally into a non-rotatable chamber.

U.S. Pat. No. 4,509,560 describes a granular material processing apparatus employing a rotating paddle to stir the granular material.

U.S. Pat. No. 2,540,059 describes a powder filling apparatus having a rotating wire loop stirrer for stirring powder in a hopper before directly pouring the powder into a metering chamber by gravity.

German patent DE 3607187 describes a mechanism for the metered transport of fine particles.

Product brochure, "E-1300 Powder Filler" describes a powder filler available from Perry Industries, Corona, Calif.

U.S. Pat. No. 3,874,431 describes a machine for filling capsules with powder. The machine employs coring tubes that are held on a rotatable turret.

British Patent No. 1,420,364 describes a membrane assembly for use in a metering cavity employed to measure quantities of dry powders.

British Patent No. 1,309,424 describes a powder filling apparatus having a measuring chamber with a piston head used to create a negative pressure in the chamber.

Canadian Patent No. 949,786 describes a powder filling machine having measuring chambers that are lipped into the powder. A vacuum is then employed to fill the chamber with powder.

SUMMARY OF THE INVENTION

The invention provides systems, apparatus and methods for the metered transport of fine powders into unit dose receptacles. In one exemplary method, such fine powders are transported by first agitating the fine powders with a vibrating element, and then capturing at least a portion of the fine powder. The captured fine powder is then transferred to a receptacle, with the transferred powder being sufficiently uncompacted so that it can be substantially dispersed upon removal from the receptacle. Usually, the fine powder will comprise a medicament with the individual particles having a mean size that is less than about 100 μm, usually less than about 10 μm, and more usually in the range from about 1 μm to 5 μm.

The fine powder will preferably be placed into a hopper having an opening at a bottom end. The element is vibrated to agitate the fine powder. Vibration of the powder in the vicinity of the opening assists in the transfer of a portion of the fine powder through the opening where it may be captured into a chamber. Vibration of the element also assists in de-agglomerating powder within the metering chamber so that the metering chamber may more uniformly be filled.

The vibratable element is preferably vibrated in an up and down, i.e. vertical, motion relative to the powder in the hopper. In one aspect, an ultrasonic horn is employed to vertically vibrate the element. Alternatively, the element may comprise a rod that is vibrated back and forth, i.e. laterally, within the powder. In another alternative, the vibratable element is vibrated in an orbital manner. In one aspect, the rod is operably attached to a piezoelectric motor which vibrates the rod. Preferably, the element is vertically vibrated at a frequency in the range from about 1,000 Hz to about 180,000 Hz, and more preferably from about 10,000 Hz to about 40,000 Hz, and most preferably from about 15,000 Hz to about 25,000 Hz. The rod is preferably vibrated laterally at a frequency in the range from about 50 Hz to about 50,000 Hz, and more preferably in the range from about 50 Hz to about 5,000 Hz, and most preferably in the range from about 50 Hz to about 1,000 Hz.

In another aspect, the element has a distal end which is placed near the opening. Further, the distal end has an end member which is vibrated over the chamber to assist in transfer of the fine powder from the hopper to the chamber. The end member preferably projects laterally outward from the element. In one aspect, the end member comprises a cylinder when the element is vibrated vertically. In another aspect, the end member comprises a cross-member when the rod is laterally vibrated. Preferably, the end-member is vertically spaced apart from the chamber by a distance in the range from about 0.01 mm to about 10 mm, and more preferably from about 0.5 mm to about 3.0 mm. Such a distance assists in keeping the powder uncompacted when transferred to the chamber.

In still another aspect, the element is preferably moved across the opening while being vibrated. For instance, the element may be translated along the opening at a rate that is preferably less than about 100 cm/s. However, the particular rate of translation will typically depend on the vibrational frequency of the element. In this way, the element is swept across the chamber while being vibrated.

Movement of the element along the opening is particularly preferable when multiple chambers are aligned with the opening. In this way, the element may be employed to assist in the transfer of fine powder from the hopper into each of the chambers. Optionally, a plurality of elements or rods may be vibrated within the hopper in the vicinity of the openings. Preferably, the rods will be aligned with each other and will be translated along the opening while being vibrated, although in some cases the rods or elements may remain stationary over each chamber.

To assist in the capture of the fine powder in the chamber, air is preferably drawn through the chamber bottom to draw the fine powder into the chamber. Following capture of the fine powder, the powder is preferably transferred to a receptacle. Transferring of the fine powder is preferably accomplished by introducing a compressed gas into the chamber to expel the captured powder into the receptacle.

In another aspect of the method, the powder in the hopper is periodically levelled. As one example, the powder may be levelled by placing a projecting member above the distal end of the vibratable element. In this way, the projecting member vibrates along with the vibratable element. As the element is translated along the hopper, the projecting member tends to level the powder in the hopper. In one aspect, transfer of the powder is performed in a moisture controlled environment.

In still another aspect, the powder captured by the chamber is adjusted to be a unit dose amount. This may be accomplished by placing a thin plate (or doctor sheet) between the hopper and the chamber. The plate has an aperture to allow for the transfer of the powder from the hopper and into the chamber. The chamber is then moved relative to the plate, with the plate scraping any excess powder from the chamber. Alternatively, a doctor blade may be employed to scrape any excess powder from the chamber as the chamber is rotated.

In one particular aspect, the powder is transferred to the hopper from a secondary hopper. Preferably, the secondary hopper is vibrated to transfer the powder onto a chute where it passes into the primary hopper. In still yet another aspect, the chamber is periodically removed and replaced with a chamber of a different size to adjust the volume of the chamber. In this way, different unit dosages may be produced by the invention.

The invention further provides an exemplary apparatus for transporting a fine powder. The apparatus comprises a hopper for holding the fine powder. The apparatus further includes at least one chamber which is moveable to allow the chamber to be placed in close proximity to an opening in the hopper. A vibratable element is also provided having a proximal end and a distal end, with the element being placed within the hopper such that the distal end is near the opening. A vibrator is provided to vibrate the element when within the fine powder. In this way, the element may be vibrated to agitate the fine powder to assist in its transfer from the hopper to the chamber. Preferably, the vibrator comprises an ultrasonic horn which vibrates the element in an up and down or vertical motion. Alternatively, a piezoelectric motor may be employed to laterally vibrate the element.

In one exemplary aspect, the apparatus further includes a mechanism for translating the vibratable element or rod over the chamber as the element is vibrated. Such a mechanism is particularly advantageous when a plurality of chambers are provided in a rotatable member which is rotated to align the chambers with the opening. The translating mechanism may then be employed to translate the element over the rotatable member so that the vibrating element passes over each chamber to assist in the filling of each with powder. The translating mechanism preferably comprises a linear drive mechanism which translates the rod along the opening at a rate that is less than about 100 cm/s.

In another aspect, the vibrator is configured to vibrate the element in an up and down motion at a frequency in the range from about 1,000 Hz to about 180,000 Hz, and more preferably in the range from about 10,000 Hz to about 40,000 Hz, and most preferably in the range from about 15,000 Hz to about 25,000 Hz. When vibrated up and down, the vibratable element preferably comprises a cylindrical shaft having a diameter in the range from about 1.0 mm to about 10 mm. When vibrated laterally, the element preferably comprises a rod or wire having a diameter in the range from about 0.01 inch to about 0.04 inch.

An end-member is preferably operably attached to the distal end of the vibratable element to assist in agitation of the fine powder. The end-member is preferably vertically spaced apart from the chamber by a distance in the range from about 0.01 mm to about 10 mm, and more preferably from about 0.5 mm to about 3.0 mm. In one alternative, the apparatus is provided with a plurality of vibratable elements so that multiple elements may be vibrated within the fine powder.

In still another aspect, the chamber is disposed within a rotatable member which is placed in a first position having the chamber aligned with the opening in the hopper, and a second position having the chamber aligned with a receptacle. In this way, the chamber may be filled with powder when in the first position. The rotatable member is then rotated to the second position to allow the powder to be expelled from the chamber and into the receptacle. The chamber preferably includes a port which is in communication with a vacuum source to assist in drawing the fine powder from the hopper and into the chamber. A filter is preferably disposed across the port to assist in capturing the powder. A source of compressed gas is preferably also in communication with the port to eject the captured powder from the chamber and into the receptacle. A controller may be provided for controlling actuation of the gas source, the vacuum source and operation of the vibrator.

The apparatus may also include a mechanism for adjusting the amount of captured powder in the chamber due to the chamber volume. In this way, the captured amount will be a unit dose amount. Such an adjustment mechanism may comprise an edge for removing fine powder extending above the chamber. In one embodiment, the adjustment mechanism comprises a thin plate having an aperture which may be aligned with the chamber during filling. As the rotatable member is rotated, the edge of the aperture scrapes the excess powder from the chamber.

In one particular aspect, the vibratable element includes a projecting member which is spaced above the distal end. The projecting member serves as a leveller to level powder within the hopper as the vibratable element is translated along the hopper.

In another aspect, a secondary hopper is provided to store the powder until delivered to the primary hopper. A shaking mechanism is provided to vibrate the secondary hopper when powder is to be transferred to the primary hopper. Preferably, the powder passes down a chute so that the powder may be transferred without interfering with the translation of the vibratable member along the primary hopper.

In still another aspect, the chamber is formed in a change tool. In this way, the size of the chamber may be varied simply by attaching a change tool with a different sized chamber to the rotatable member.

The invention further provides an exemplary system for transporting fine powders. The system comprises a plurality of rotatable members which each include a row of chambers. A hopper is disposed above each rotatable member and has an opening to allow powder to be transferred to the chambers. A vibratable element is disposed in each hopper, and vibrators are provided to vibrate the elements in an up and down motion. A translation mechanism is further provided to translate the vibratable members along the hoppers to assist in transferring the powder from the hoppers and into the chambers. Conveniently, a controller may be provided to control operation of the rotatable members, the vibrators, and the translation mechanism.

DETAILED DESCRIPTION OF THE SPECIFIC EMBODIMENTS

Figure 1:
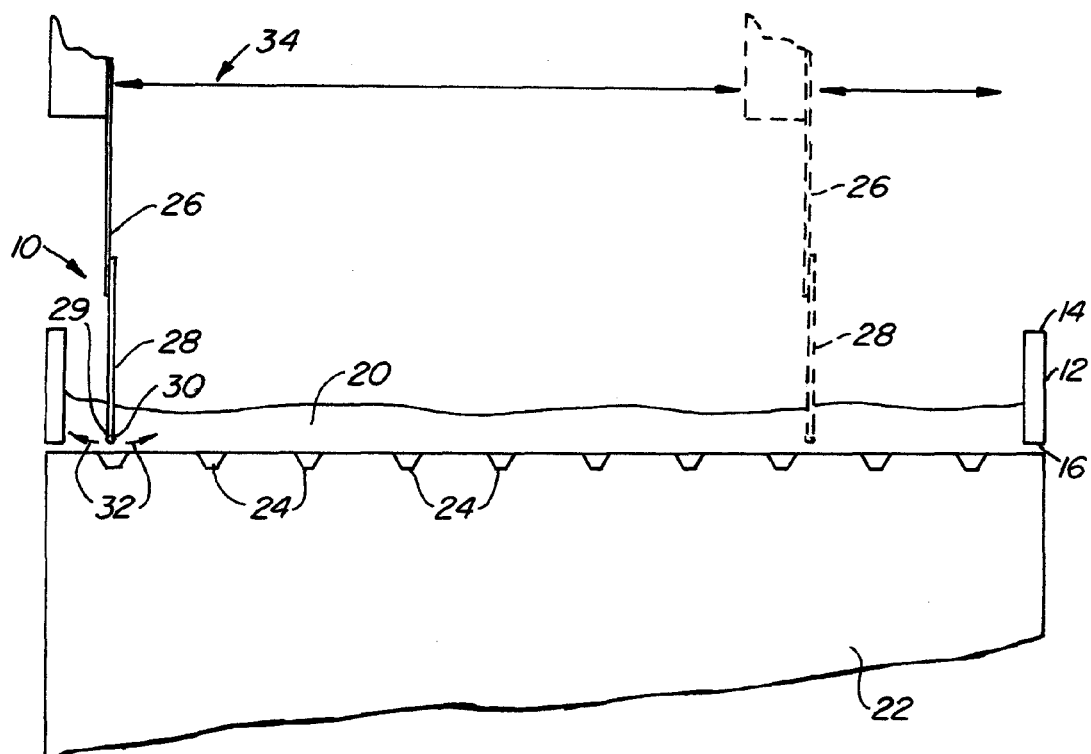
FIG. 1 is a cross-sectional side view of an exemplary apparatus for transporting fine powders according to the invention.

The invention provides methods, systems, and apparatus for the metered transport of fine powders into receptacles. The fine powders are very fine, usually having a mean size in the range that is less than about 20 µm, usually less than about 10 µm, and more usually from about 1 µm to 5 µm, although the invention may in some cases be useful with larger particles, e.g., up to about 50 µm or more. The fine powder may be composed of a variety of constituents and will preferably comprise a medicament such as proteins, nucleic acids, carbohydrates, buffer salts, peptides, other small biomolecules, and the like. The receptacles intended to receive the fine powder preferably comprise unit dose receptacles. The receptacles are employed to store the unit dosage of the medicament until needed for pulmonary delivery. To extract the medicament from the receptacles, an inhalation device, such as those described in U.S. Pat. Nos. 5,785,049 and 5,740,794, previously incorporated herein by reference, may be employed. However, the methods of the invention are also useful in preparing powders to be used with other inhalation devices which rely on the dispersement of the fine powder.

The receptacles are preferably each filled with a precise amount of the fine powder to ensure that a patient will be given the correct dosage. When metering and transporting the fine powders, the fine powders will be delicately handled and not compressed, so that the unit dosage amount delivered to the receptacle is sufficiently dispersible to be useful when used with existing inhalation devices. The fine powders prepared by the invention will be especially useful with, although not limited to, "low energy" inhalation devices which rely on manual operation or solely upon inhalation to disperse the powder. With such inhalation devices, the powder will preferably be at least 20% (by weight) dispersible or extractable into a flowing air stream, more preferably be at least 60% dispersible, and most preferably at least 90% dispersible as defined in U.S. Pat. No. 5,785,049, previously incorporated by reference. Since the cost of producing the fine powder medicaments are usually quite expensive, the medicament will preferably be metered and transported into the receptacles with minimal wastage. Preferably, the receptacles will be rapidly filled with the unit dosage amounts so that large numbers of receptacles containing the metered medicament can economically be produced.

According to the invention, the fine particles are captured in a metering chamber (which is preferably sized to define a unit dosage volume). A preferable method of capturing is by drawing air through the chamber so that the drag force of the air will act upon the small agglomerates or individual particles as described in U.S. Pat. No. 5,775,320, the complete disclosure of which is herein incorporated by reference. In this way, the fluidized fine powder fills the chamber without substantial compaction and without substantial formation of voids. Further, capturing in this manner allows the fine powder to be accurately and repeatably metered without unduly decreasing the dispersibility of the fine powder. The flow of air through the chamber may be varied in order to control the density of the captured powder.

After the fine powder is metered, the fine powder is ejected into the receptacle in a unit dosage amount, with the ejected fine powder being sufficiently dispersible so that it may be entrained and aerosolized in the turbulent air flow created by an inhalation or dispersion device. Such an ejection process is described in U.S. Pat. No. 5,775,320, previously incorporated by reference.

Agitation of the fine powders is preferably accomplished by vibrating a vibratable member within the fine powder in the vicinity just above the capture chamber. Preferably, the element is vibrated in an up and down, i.e., vertical, motion. Alternatively, the element may be laterally vibrated. A variety of mechanisms may be employed to vibrate the elements including an ultrasonic horn, a piezoelectric bending motor, a motor rotating a cam or a crank shaft, an electric solenoid, and the like. Alternatively, a wire loop may be rotated within the fine powder to fluidize the powder. Although agitation is preferably accomplished by vibrating the vibratable member within the fine powder, in some cases it may be desirable to vibrate the vibratable member just above the powder to fluidize the powder.

Figure 2:
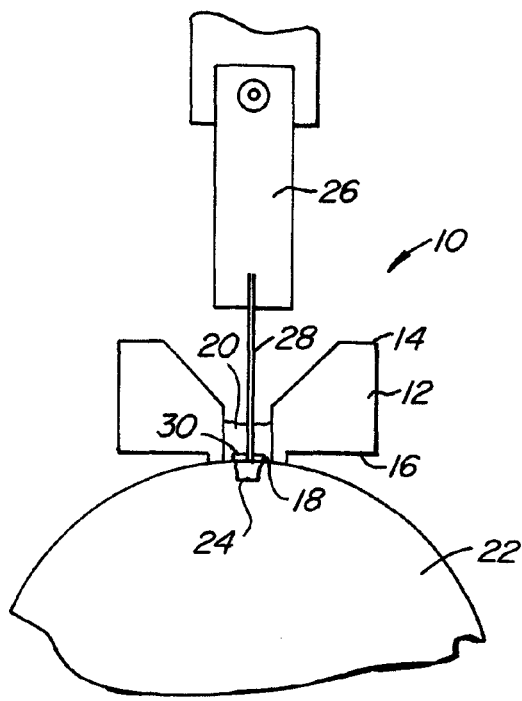
FIG. 2 is an end view of the apparatus of FIG. 1.

Referring to FIGS. 1 and 2, an exemplary embodiment of an apparatus 10 for metering and transporting unit dosages of a fine powder medicament will be described. Apparatus 10 comprises a trough or hopper 12 having a top end 14 and a bottom end 16. At bottom end 16 is an opening 18. Held within hopper 12 is a bed of fine powder 20. Positioned below hopper 12 is a rotatable member 22 having a plurality of chambers 24 about its periphery. Rotatable member 22 may be rotated to align chambers 24 with opening 18 to allow powder 20 to be transferred from hopper 12 and into chambers 24.

Positioned above hopper 12 is piezoelectric bending motor 26 having a rod 28 attached thereto. Piezoelectric motor 26 is positioned above hopper 12 such that a distal end 29 of rod 28 is placed within the fine powder bed 20 while being spaced apart from rotatable member 22. Bottom end 16 of hopper 12 is positioned just above rotatable member 22 so that powder held within hopper 12 will not escape between bottom end 16 and rotatable member 22. At distal end 29 of rod 28 is a cross-member 30 which is generally perpendicular to rod 28. Cross-member 30 will preferably be at least as long as the top diameters of chambers 24 to assist in agitating fine powder into the chambers as described in greater detail hereinafter.

As best illustrated in FIG. 1, upon actuation of piezoelectric bending motor 26, rod 28 is caused to vibrate back and forth as indicated by arrows 32. Further, as illustrated by arrow 34, piezoelectric bending motor 26 is translatable along the length of rotatable member 22 to allow cross-member 30 to be vibrated over each of the chambers 24.

Figure 3:
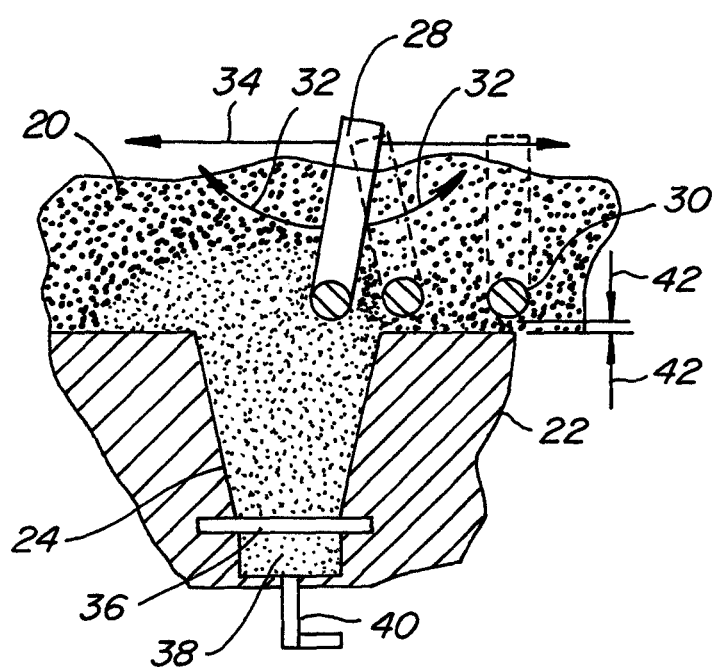
FIG. 3 is a more detailed view of a chamber of the apparatus of FIG. 1 showing a vibrating rod being translated over the chamber according to the invention.

Referring now to FIG. 3, the transfer of powder from hopper 12 (see FIG. 1) to chamber 24 will be described in greater detail. Disposed within chamber 24 is a top filter 36 and a back-up filter 38. Top filter 36 is disposed in rotatable member 22 such that it is at a known distance relative to the top of chamber 24. A line 40 is in communication with chamber 24 to provide suction within chamber 24 during filling and compressed gas when expelling the powder from chamber 24 in a manner similar to that described in copending U.S. patent application Ser. No. 08/638,515, the disclosure of which is herein incorporated by reference.

When ready for filling, a vacuum is created within line 40 to draw air through chamber 24. Further, rod 28 is vibrated as shown by arrows 32 when positioned above chamber 24 to assist in agitating powder bed 20. Such a process assists in transferring the powder from bed 20 and into chamber 24. While vibrating, rod 28 is translated over chamber 24 as indicated by arrow 34. In this way, agitation of the powder bed 20 will occur over substantially the entire opening of the chamber 24. Further, translation of rod 28 will also move rod 28 over other chambers so that they may be filled in a similar manner.

Figure 4:
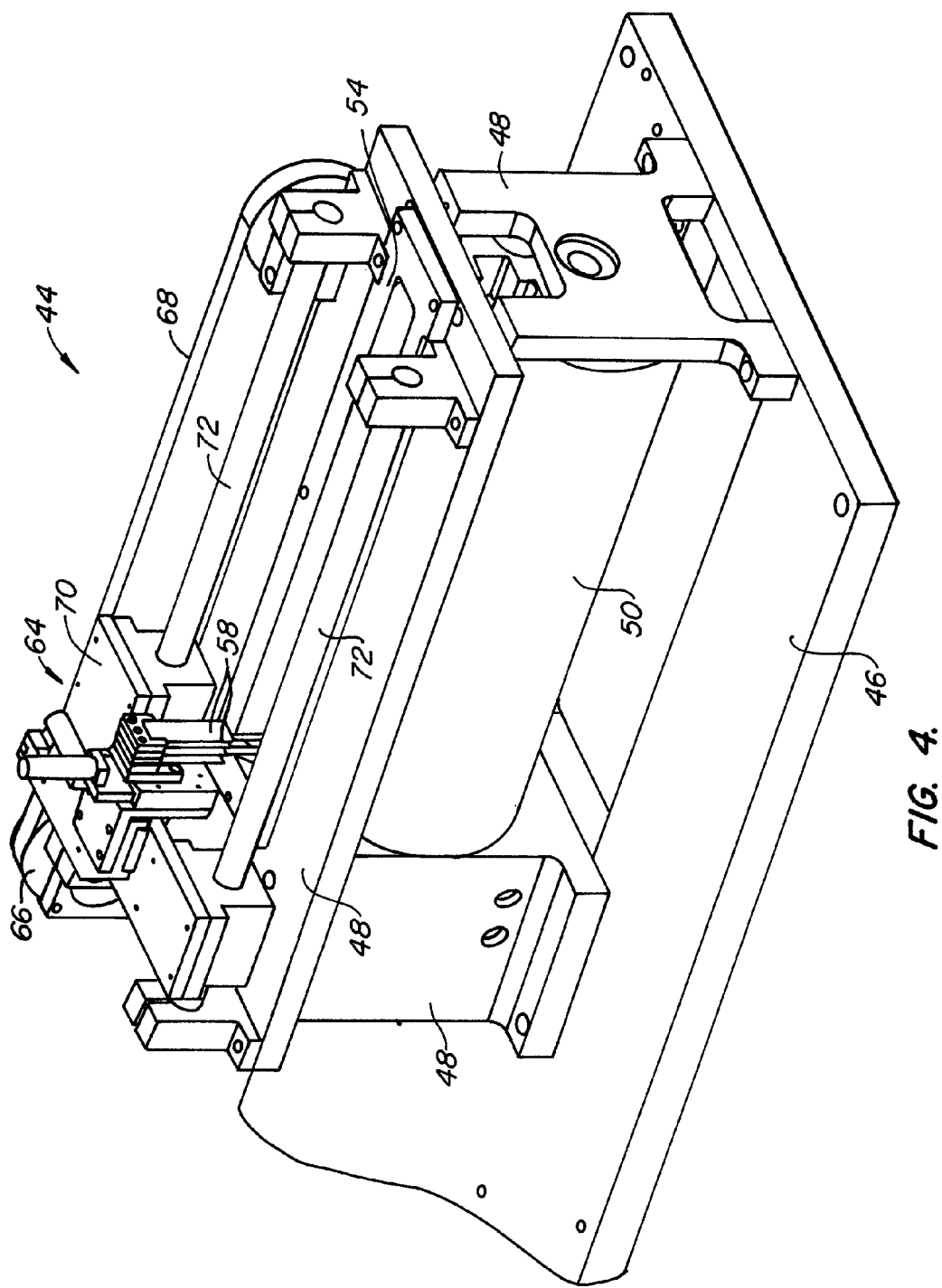
FIG. 4 is a left front perspective view of an exemplary system for transporting powder according to the invention.
Figure 5:
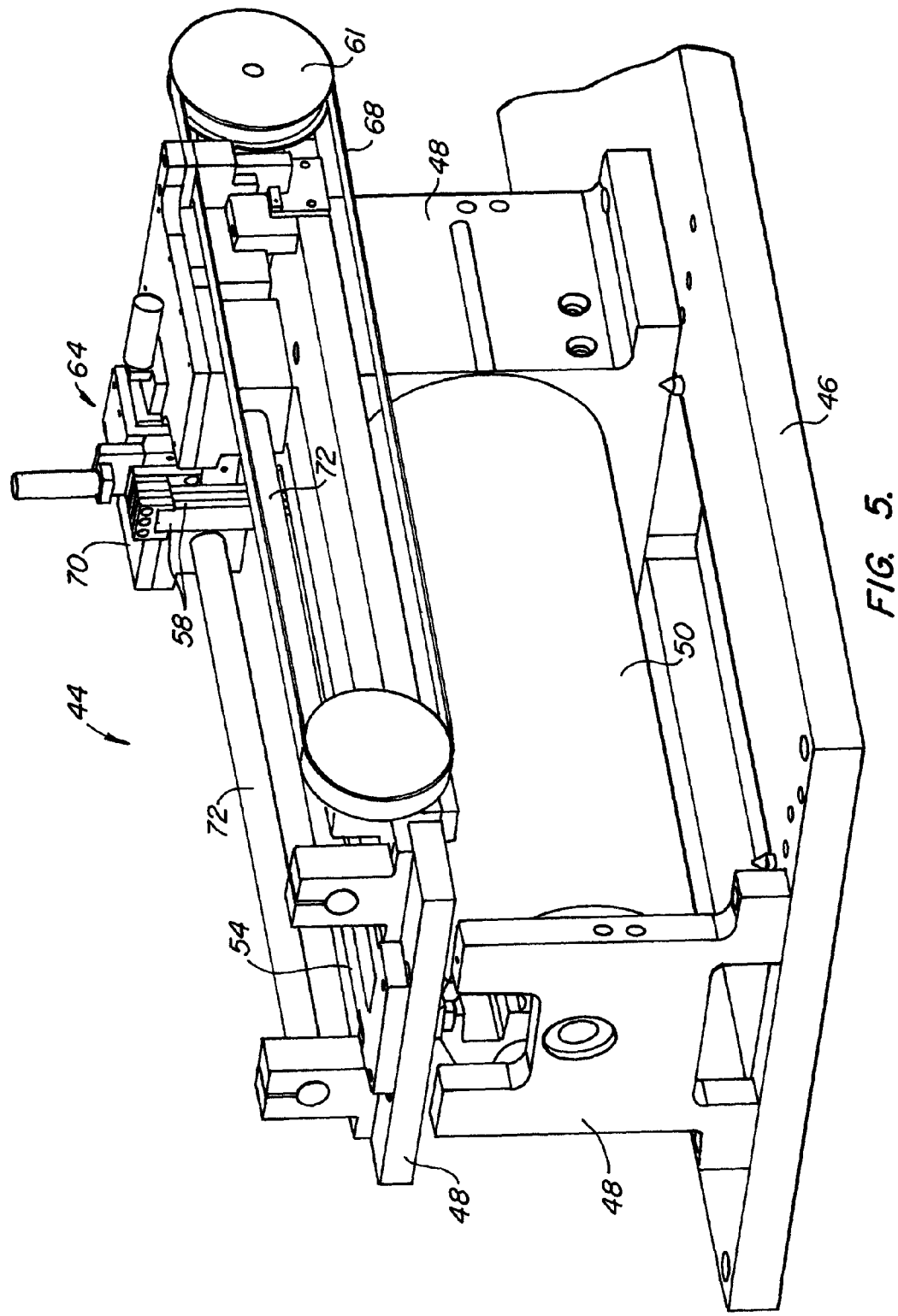
FIG. 5 is a right front perspective view of the system of FIG. 4.
Figure 6:
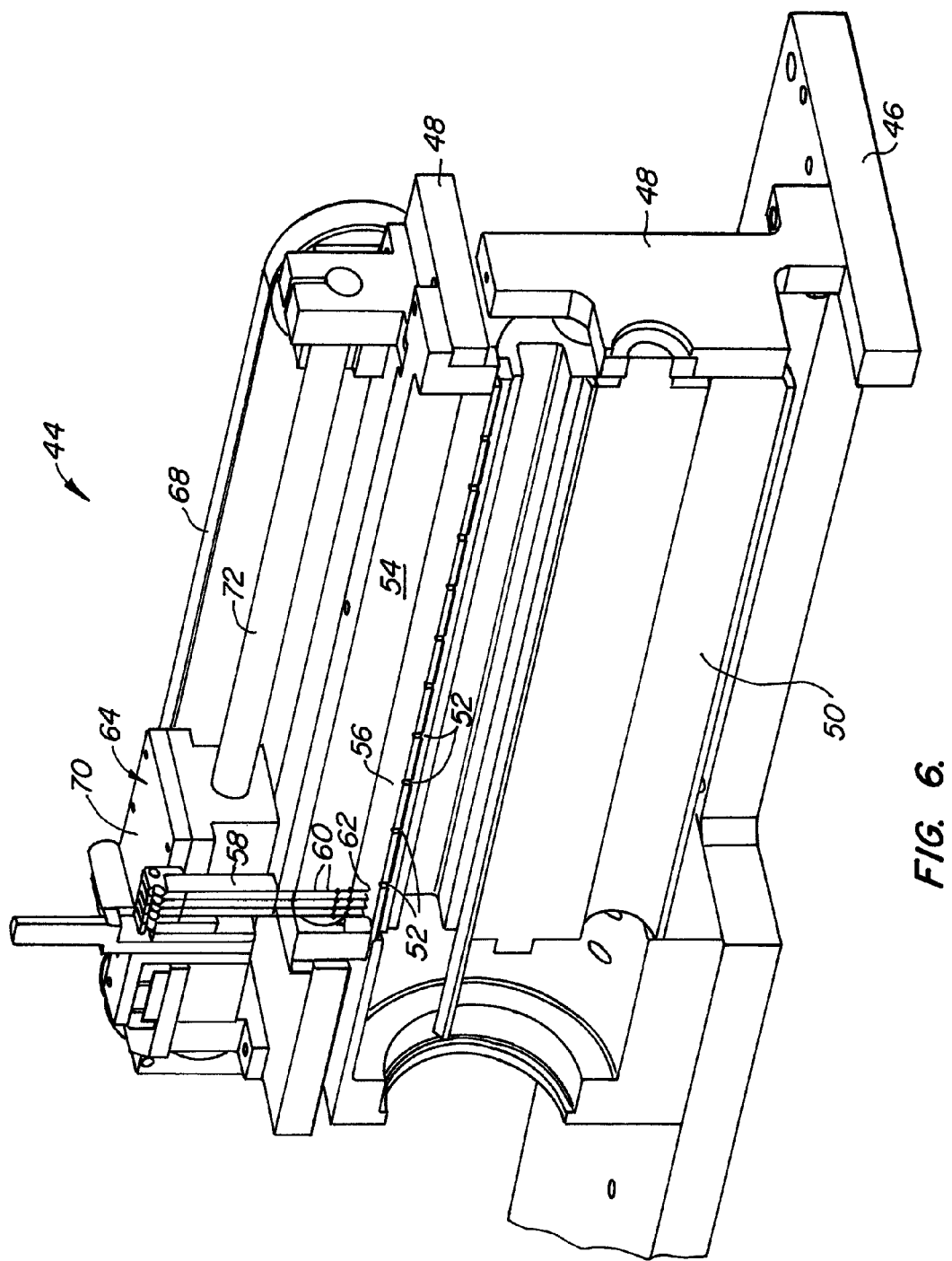
FIG. 6 is a cross-sectional view of the system of FIG. 4.

As illustrated by arrows 42, rod 28 will preferably be vertically spaced from rotatable member 22 by a distance in the range from about 0.01 mm to about 10 mm, and more preferably from about 0.1 mm to about 0.5 mm. Such vertical spacing is preferred to ensure that the powder immediately above the cavity is fluidized and can be drawn into the chamber 24. Referring now to FIGS. 4-6, an exemplary embodiment of a powder transferring and metering system 44 will be described. System 44 is patterned after the principles previously set forth in connection with apparatus 10 of FIGS. 1-3. System 44 comprises a base 46 and a frame 48 for rotatably holding a rotatable member 50. Rotatable member 50 includes a plurality of chambers 52 (see FIG. 6). Rotatable member 50, including chambers 52, will preferably be provided with vacuum and compression lines similar to that previously described in copending U.S. patent application Ser. No. 08/638,515, previously incorporated by reference. In brief, a vacuum is created to assist in drawing powder into chambers 52. Upon filling of chambers 52, rotatable member 50 is rotated until chambers 52 are facing downward. At that point, compressed gas is forced through chambers 52 to eject the captured powder into receptacles, such as blister packages as are commonly used in the art.

Positioned above rotatable member 50 is a hopper 54 having an elongate opening 56 (see FIG. 6). Operably mounted to frame 48 are a plurality of piezoelectric bending motors 58. Attached to each of piezoelectric bending motors 58 is a rod 60. An exemplary piezoelectric bending motor is commercially available from Piezo Systems, Inc., Cambridge, Mass. Such bending motors comprise two layers of a piezoceramic, each having an outer electrode. An electric field is applied across the two outer electrodes to cause one layer to expand while the other contracts.

Rod 60 will preferably comprise a stainless steel wire rod having a diameter in the range from about 0.005 inch to about 0.10 inch, and more preferably from about 0.02 inch to about 0.04 inch. However, it will be appreciated that other materials and geometries may be used when constructing rod 60. For example, a variety of rigid materials may be employed, including other metals and alloys, a steel music wire, a carbon fiber, plastics, and the like. The shape of rod 60 may also be non-circular and/or non-uniform in cross section, with an important feature being the ability to agitate the powder near the distal end of the rod to fluidize the powder. A perpendicular cross-member 62 (see FIG. 6) will preferably be attached to the distal end of rod 60. One or more cross-members may optionally be positioned above the distal cross-member to help collapse any trenches created in the powder bed during operation. When actuated, rods 60 will preferably be vibrated at a frequency in the range from about 5 Hz to about 50,000 Hz, and more preferably in the range from about 50 Hz to about 5,000 Hz, and most preferably in the range from about 50 Hz to about 1,000 Hz.

Piezoelectric bending motors 58 are attached to translation mechanism 64 which translates rods 60 along hopper 54. When translated, cross-member 62 will preferably be vertically spaced above chambers 52 by a distance in the range from about 0.01 mm to about 10 mm, and more preferably from about 0.1 mm to about 0.5 mm. Translation mechanism 64 comprises a rotary drive pulley 66 which rotates a belt 68, which in turn is attached to a platform 70. Piezoelectric bending motors 58 are attached to platform 70 which is translated over a shaft 72 when pulley 66 is actuated. In this way, rods 60 may be translated back and forth within hopper 54 so that rods 60 will be vibrated over each of the chambers 52. Translation mechanism 64 may be employed to pass rod 60 over chambers 52 as many times as desired when filling chambers 52. Preferably, rod 60 will be translated at a speed that is less than about 200 cm/s, and more preferably less than about 100 cm/s. Rod 60 will preferably pass over each chamber at least one time, with two passes being preferred.

In operation, hopper 54 is filled with fine powder that is to be transferred into chambers 52. A vacuum is then drawn through each of chambers 52 while they are aligned with opening 56. At the same time, piezoelectric bending motors 58 are actuated to vibrate rods 60. Translation mechanism 64 is actuated to translate rods 60 back and forth within hopper 54 while rods 60 are vibrating. Vibration of rods 60 agitates the fine powder to assist in its transfer into chambers 52. When chambers 52 are sufficiently filled, rotatable member 50 is rotated 180° to place chambers 52 in a downward position. As rotatable member 50 is rotated, a blade at the bottom edge of hopper 54 scrapes off any excess powder to ensure that each chamber contains only a unit dose amount of fine powder.

When in the downward position, a compressed gas is forced through each of chambers 52 to eject the fine powder into receptacles (not shown). In this way, a convenient method is provided for transferring fine powder from a hopper into receptacles in a metered amount.

Figure 7:
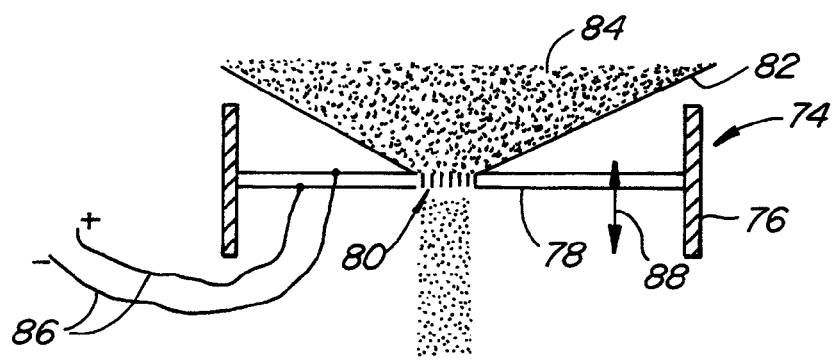
FIG. 7 is a schematic view of an alternative apparatus for transporting fine powders according to the invention.

Referring now to FIG. 7, an alternative embodiment of an apparatus 74 for transferring metered doses of fine powder will be described. Apparatus 74 comprises a housing 76 and a piezo substrate 78 operably attached to housing 76 piezo substrate 78 includes a plurality of holes 80 (or a screen). Positioned above substrate 78 is a hopper 82 having a bed of fine powder 84. Attached to substrate 78 is a pair of electrical leads 86 for actuation of piezo substrate 78. When electrical current is alternately supplied to leads 86, substrate 78 is caused to expand and contract to produce a vibration mode as illustrated by arrow 88. In turn, holes 80 are caused to vibrate to assist in agitating powder bed 84 to more effectively allow the powder to fall through holes 80 and into a chamber. A rotatable member having chambers in communication with a vacuum source and a pressure source as described in previous embodiments may also be used in connection with apparatus 74 to assist in capturing the fine powder and expelling the captured powder into receptacles.

Figure 8:
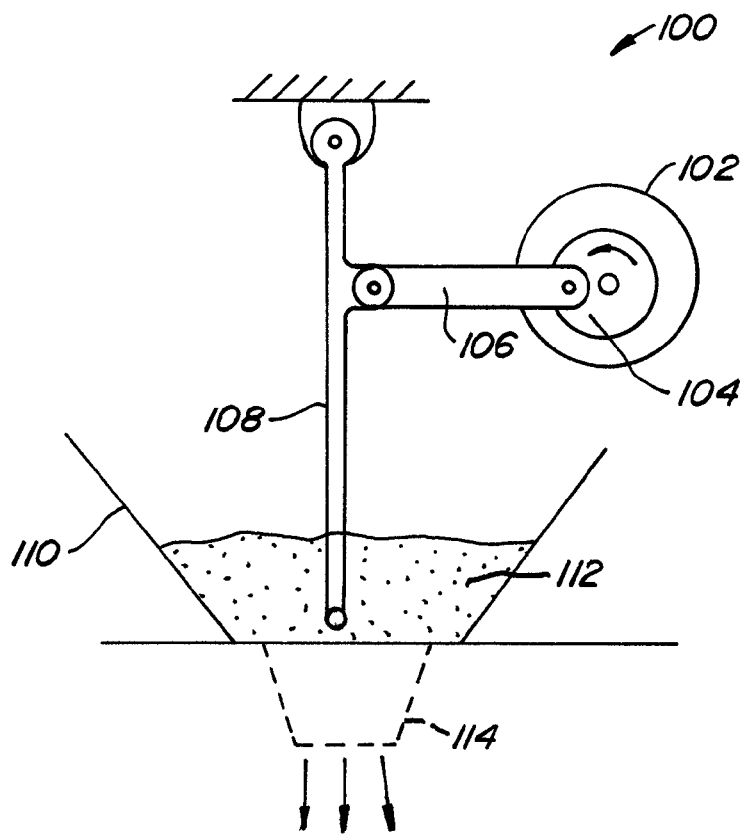
FIG. 8 is a schematic view of still another alternative apparatus for transporting fine powders according to the invention.

A further embodiment of an apparatus 100 for transferring metered doses of fine powder is illustrated in FIG. 8. Apparatus 100 operates similar to apparatus 10 as previously described, except that the piezoelectric bending motor has been replaced with a motor 102 having a crank 104 which drives a linkage shaft 106. As shaft 106 is reciprocated, a rod 108 is vibrated within a hopper 110 that is filled with powder 112. The agitated powder is then captured in a chamber 114 in a manner similar to that previously described. Further, rod 108 may be translated over chamber 114 during vibration in a manner similar to that previously described with other embodiments.

Figure 9:
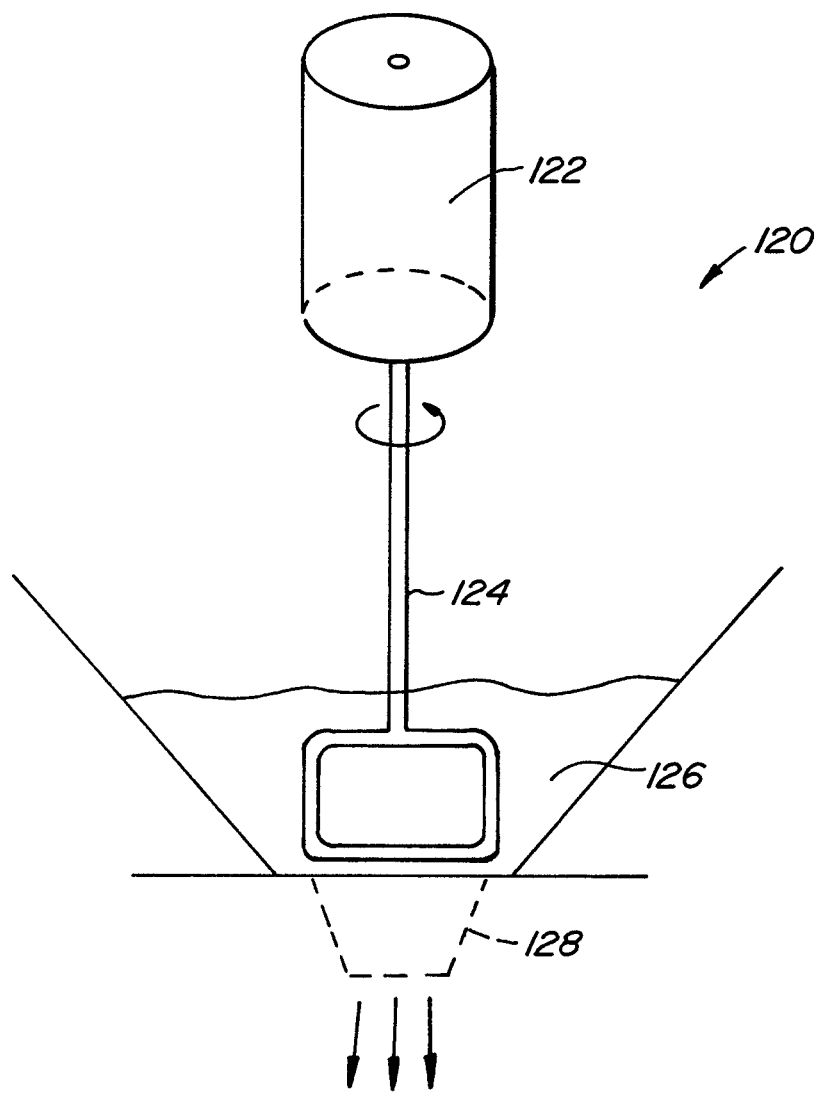
FIG. 9 is a schematic view of still another alternative apparatus for transporting fine powders according to the invention.

Another embodiment of an apparatus 120 for transferring metered doses of fine powder is illustrated in FIG. 9. Apparatus 120 comprises a motor 122 which rotates a wire loop 124. As shown, wire loop 124 is disposed within a bed of fine powder 126 just above a chamber 128. In this way, when wire loop 124 is rotated, the powder will be fluidized and drawn into chamber 128 in a manner similar to previous embodiments. Further, loop 124 may be translated over chamber 128 during its rotation in a manner similar to that previously described with other embodiments.

Figure 10:
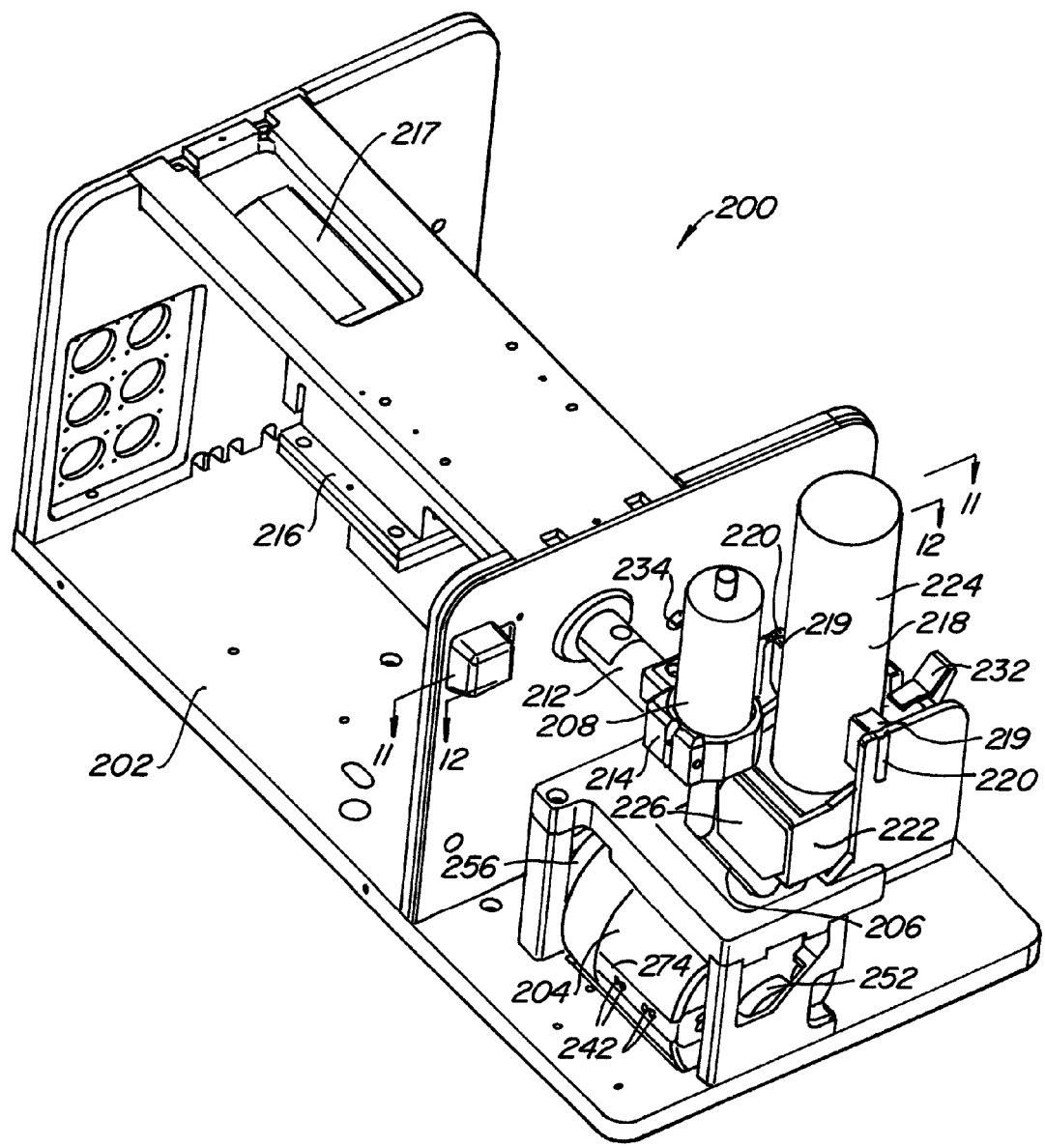
FIG. 10 is a perspective view of a further embodiment of an apparatus for transporting fine powders according to the invention.

Referring now to FIG. 10, another embodiment of an apparatus 200 for transporting fine powders will be described. Apparatus 200 operates in a manner similar to the other embodiments as previously described in that powder is transferred from a hopper into metering chambers of a rotatable member. From the rotatable member, the powder is expelled into receptacles in unit dosage amounts.

Figure 11:
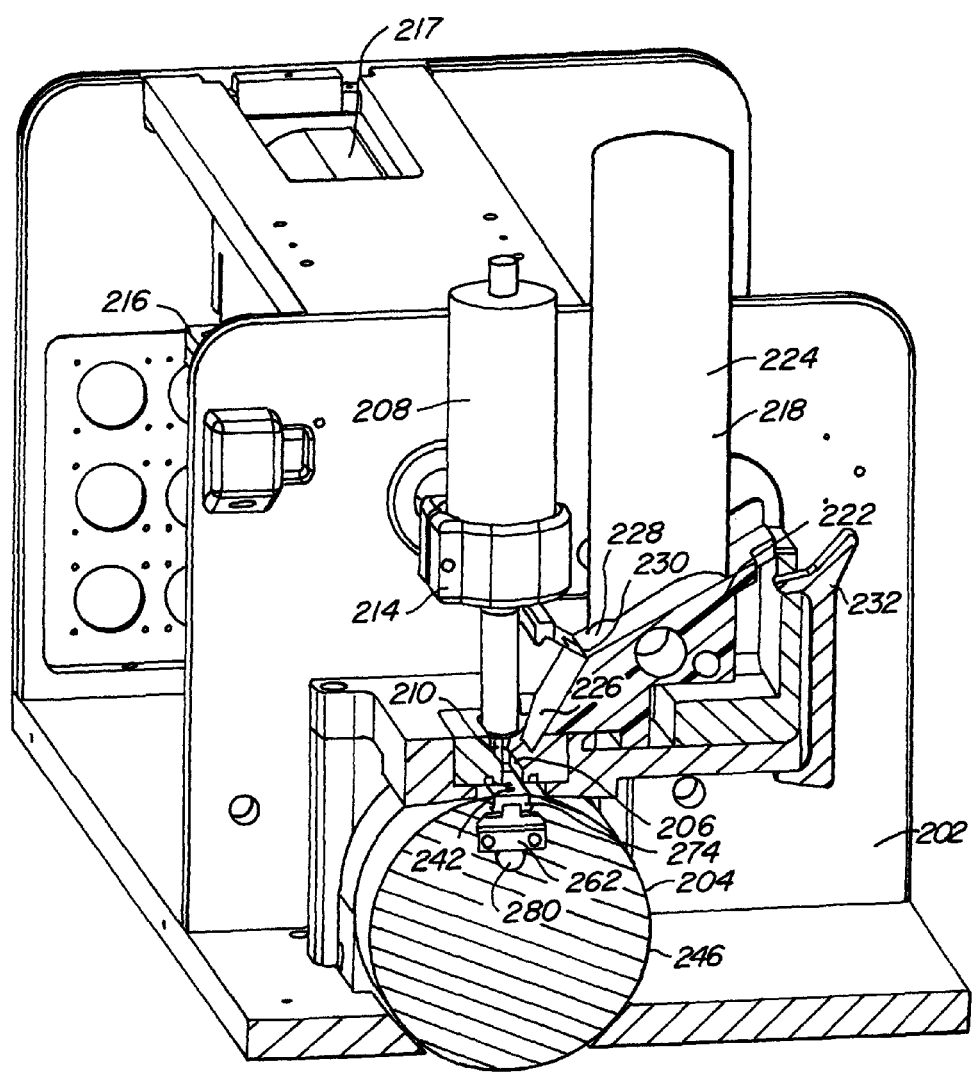
FIG. 11 is a cross-sectional view of the apparatus of FIG. 10 taken along lines 11-11.
Figure 12:
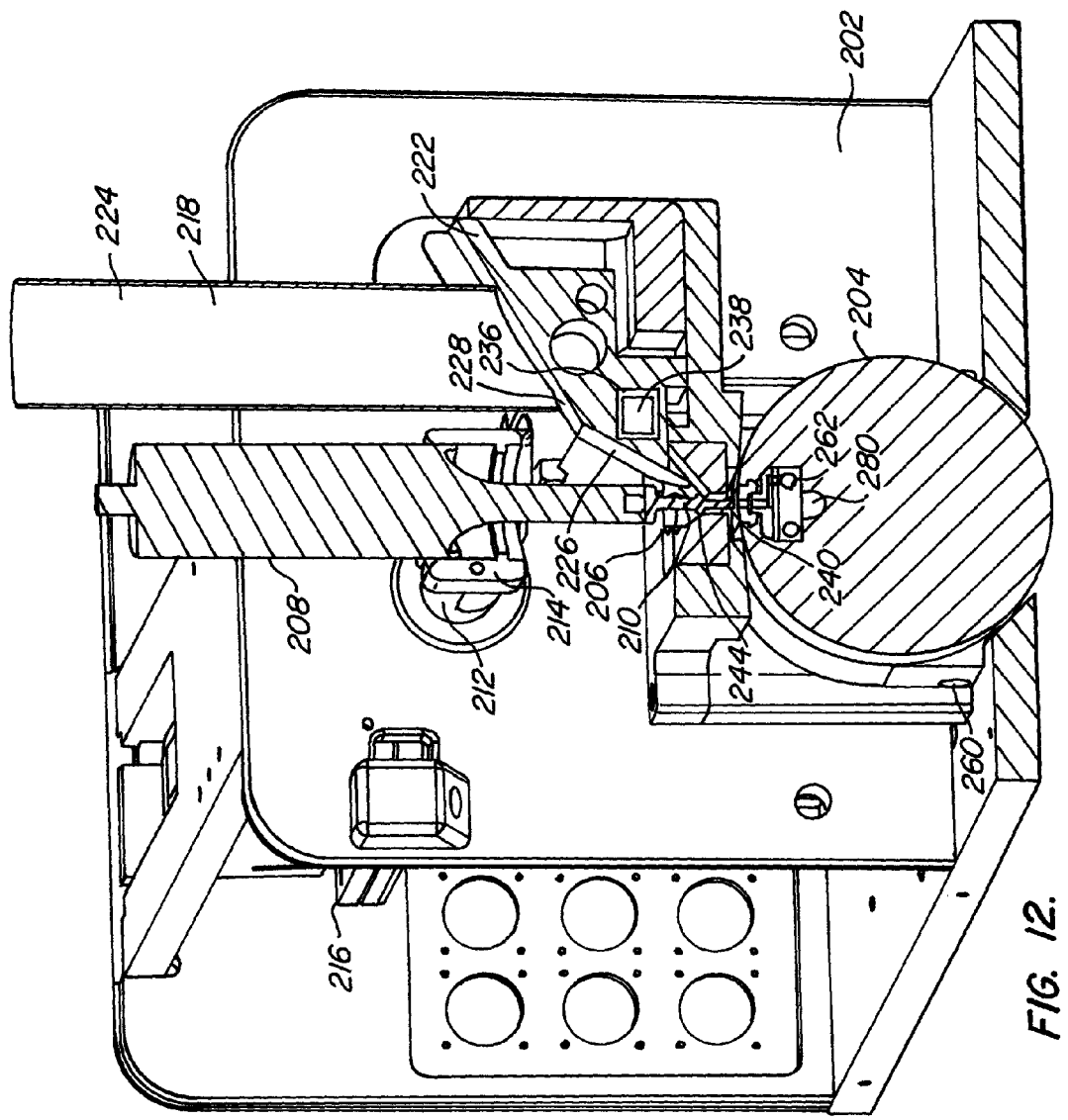
FIG. 12 is a cross-sectional view of the apparatus of FIG. 10 taken along lines 12-12.

Apparatus 200 comprises a frame 202 which holds a rotatable member 204 such that rotatable member 204 may be rotated by a motor (not shown) held on frame 202. Frame 202 also holds a trough or primary hopper 206 above rotatable member 204. Positioned above hopper 206 is a vibrator 208. As shown in FIGS. 11 and 12, a vibratable element 210 is coupled to vibrator 208. Vibrator 208 is coupled to an arm 212 by a clamp 214. Arm 212 in turn is coupled to a translation stage 216. A screw motor 217 is employed to translate stage 216 back and forth relative to frame 202. In this way, vibratable element 210 may be translated back and forth within hopper 206.

Referring also now to FIGS. 11 and 12, apparatus 200 further includes a secondary hopper 218 disposed above primary hopper 206. Conveniently, hopper 218 includes wings 219 to allow it to be removably coupled to frame 202 by inserting wings 219 into slots 220. Hopper 218 comprises a housing 222 and a tubular section 224 for storing powder. A chute 226 extends from housing 222 and into hopper 206 when hopper 218 is attached to frame 202. Tubular section 224 includes an opening 228 to allow powder to flow from tubular section 224 and down chute 226. A screen 230 is disposed over opening 228 to generally prevent the flow of powder down chute 226 until housing 222 is shaken or vibrated.

Conveniently, a latch 232 is employed to secure secondary hopper 218 to frame 202. To remove secondary hopper 218, latch 232 is disengaged from hopper 218 and hopper 218 is lifted from slots 220. In this way, hopper 218 may be conveniently removed for refilling, cleaning, replacement, or the like.

To transfer powder from hopper 218, an arm 234 is placed into contact with housing 222 and is shaken or vibrated to vibrate housing 222. A motor (not shown) is employed to shake or vibrate arm 234. As shown in FIG. 12, housing 222 may optionally include an internal opening 236 containing a block 238. As housing 222 is shaken, block 238 vibrates within opening 236. As block 238 engages the walls of housing 222, it sends shock waves through housing 222 to assist in transferring the powder from tubular section 224, through opening 228, and through screen 230. The powder then slides down chute 226 until it falls within hopper 206. Use of chute 226 is also advantageous in that it allows tubular section 224 to be laterally offset from vibrator 208 so that it will not interfere with the motion of vibrator 208. One particular advantage of including block 238 within opening 236 is that any particulate generated as block 238 is vibrated will be maintained within opening 236 and will not contaminate any of the powder.

Vibrator 208 is configured to vibrate element 210 in an up and down or vertical motion. Vibrator 208 preferably comprises any one of a variety of commercially available ultrasonic horns, such as a Branson TWI ultrasonic horn. Vibratable element 210 is preferably vibrated at a frequency and range from about 1,000 Hz to about 180,000 Hz, and more preferably from about 10,000 Hz to about 40,000 Hz, and most preferably from about 15,000 Hz to about 25,000 Hz.

As best shown in FIG. 12, vibratable element 210 includes an end member 240 which is appropriately shaped to optimize agitation of the fine powder during vibration of element 210. As shown, end member 240 has an outer periphery which is greater than that of element 210. Element 210 is preferably cylindrical in geometry and preferably has a diameter in the range from about 0.5 mm to about 10 mm. As shown, end member 240 is also cylindrical in geometry and preferably has a diameter in the range from about 1.0 mm to about 10 mm. However, it will be appreciated that vibratable element 210 and end member 240 may be constructed to have a variety of shapes and sizes. For example, vibratable element 210 may be tapered. End member 240 may also have a reduced profile to minimize the lateral movement of powder as vibrator 208 is translated through hopper 206. Preferably, end member 240 is vertically spaced above rotatable member 204 by a distance in the range from about 0.01 mm to about 10 mm, and more preferably from about 0.5 mm to about 3.0 mm.

Vibrator 208 is employed to assist in the transfer of powder into metering chambers 242 of rotatable member 204 in a manner similar to that described with previous embodiments. More specifically, motor 217 is employed to translate stage 216 so that vibratable element 210 may be translated laterally back and forth along hopper 206. At the same time, vibratable element 210 is vibrated in an up and down motion, i.e., radial to rotatable member 204, as it passes over each of metering chambers 242. Preferably, vibrator 208 is laterally translated along hopper 206 at a rate that is less than about 500 cm per second, and more preferably less than about 100 cm per second.

As vibratable element 210 is moved laterally within hopper 206, there may be a tendency for vibratable element 210 to push or plow some of the powder towards the ends of hopper 206. Such movement of the powder is mitigated by providing a radiating surface or projecting member 244 on vibratable element 210 just above an average powder depth within the hopper. In this way, accumulated powder that is higher than the average depth is preferentially mobilized and moved to areas in the hopper having a smaller powder depth. Preferably, projecting member 244 is spaced apart from end member 240 by a distance in the range from about 2 mm to about 25 mm, and more preferably from about 5 mm to about 10 mm. As an alternative, various plowing mechanisms, such as rakes, may be attached to vibrator 208 (or be separately articulatable) so that they will drag over the top of the powder to assist in leveling the powder as vibrator 208 is translated along the hopper. As another alternative, an elongate vibratory element, such as a screen, may be disposed within the powder bed to assist in levelling the powder.

As shown in FIGS. 11 and 12, rotatable member 204 is in a filling position where metering chambers 242 are aligned with hopper 206. As with the other embodiments described herein, once metering chambers 242 are filled, rotatable member 204 is rotated 180° where the powder is ejected from metering chambers 242 into receptacles. A Klockner packaging machine is preferably employed to supply apparatus 200 with a sheet containing the receptacles.

Figure 13:
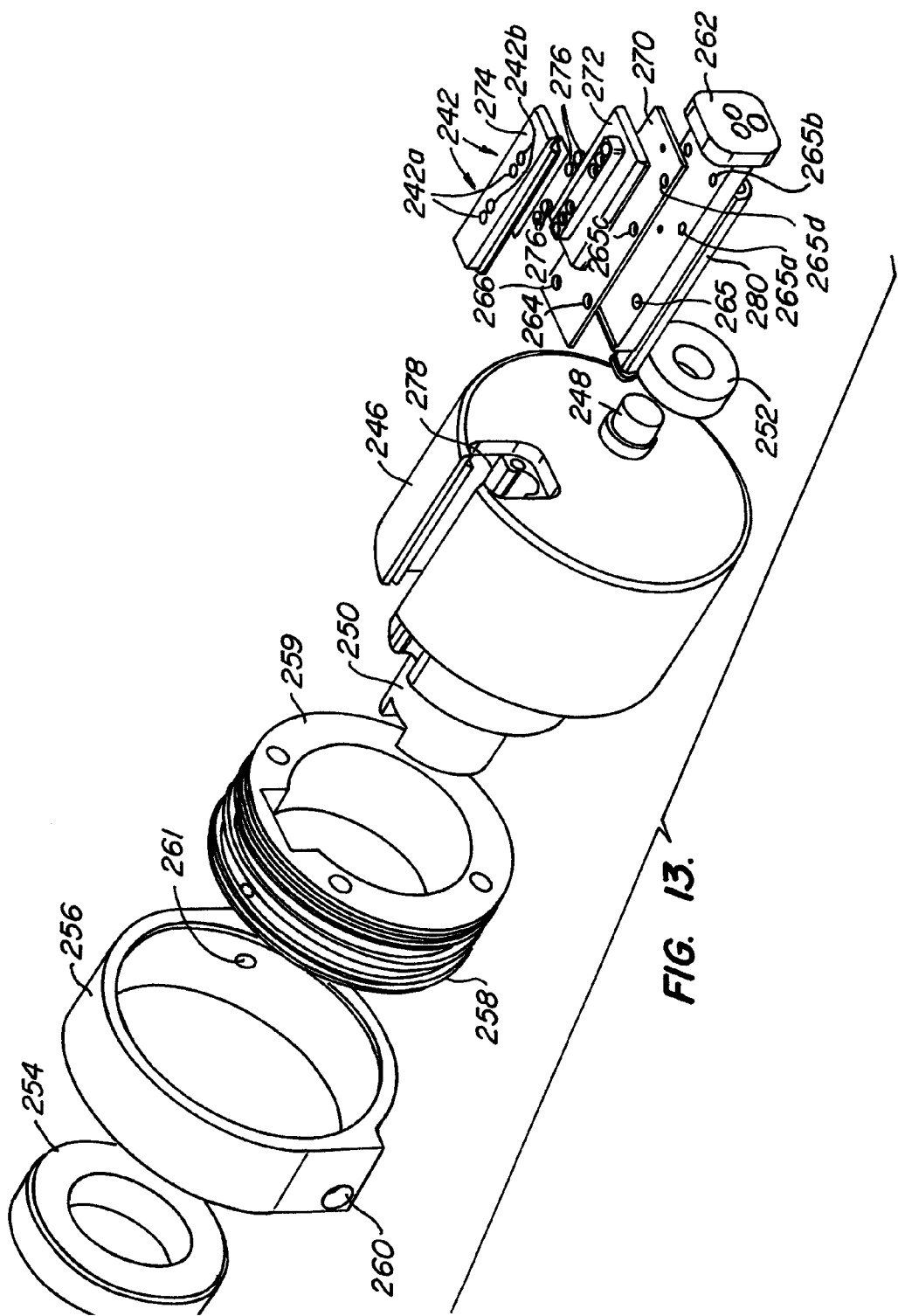
FIG. 13 is an exploded view of a rotatable member of the apparatus of FIG. 10.

Referring now to FIG. 13, construction of rotatable member 204 will be described in greater detail. Rotatable member 204 comprises a drum 246 having a front end 248 and a back end 250. Bearings 252 and 254 are insertable over ends 248 and 250 to allow drum 246 to rotate when attached to frame 202. Rotatable member 204 further includes a collar 256, a rear slip ring 258 and a front slip ring 259 which are fitted with gas tight seals. Air inlets 260 and 261 are provided in collar 256. Air inlet 260 is in fluid communication with a pair 242a of metering chambers 242 while inlet 261 is in fluid communication with a pair 242b of metering chambers 242. In this way, pressurized air or a vacuum may be produced in either pair of chambers 242a or 242b.

More specifically, air from inlet 260 passes through slip ring 258, through a hole 264 in a gasket 270 and into a hole 265 in a manifold 262. The air then passes through manifold 262 and exits manifold 262 through a pair of holes 265a and 265b. Holes 265c and 265d in bracket 272 then route the air into chambers 242a. In a similar manner, air from inlet 261 passes through slip ring 259, through a hole 266 in gasket 270 and into a hole (not shown) in manifold 262. The air is routed through various holes in manifold 262 and gasket 270 in a manner similar to that previously described with inlet 260 until passing through chambers 242b. In this manner, two separate air circuits are provided. Alternatively, it will be appreciated that one of the air inlets could be eliminated so that a vacuum or pressurized gas may be simultaneously provided to all of metering chambers 242.

Also disposed above manifold 262 is a change tool 274. Metering chambers 242 are formed in change tool 274, and filters 276 are disposed between change tool 274 and air bracket 272 to form a bottom end of metering chambers 242. Air may be drawn into chambers 242 by attaching a vacuum to air inlets 260 or 261. Similarly, a compressed gas may be forced through metering chambers 242 by coupling a source of compressed gas to air inlets 260 or 261. As with other embodiments described herein, a vacuum is drawn through metering chambers 242 to assist in drawing the powder into metering chambers 242. After drum 246 is rotated 180°, a compressed gas is forced through metering chambers 242 to expel the powder from metering chambers 242.

Drum 246 includes an aperture 278 into which manifold 262, gasket 270, air bracket 272 and change tool 274 are inserted. A cam 280 is also provided and is insertable into aperture 278. Cam 280 is rotated within aperture 278 to secure the various components within drum 246. When loosened, it is possible to slide change tool 274 from aperture 278. In this way, change tool 274 may easily be replaced with another change tool having different sized metering chambers. In this manner, apparatus 200 may be provided with a wide assortment of change tools which allows a user to easily change the size of the metering chambers simply by inserting a new change tool 274.

Figure 14A:
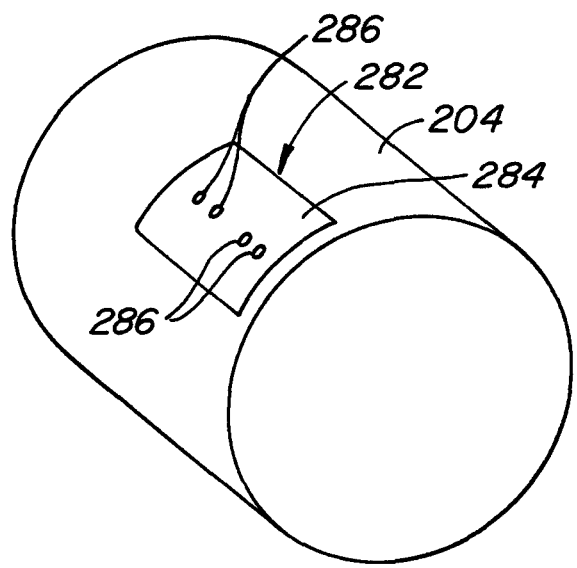
FIG. 14A is a schematic view of a scraping mechanism for scraping excess powder from a chamber of a rotatable member.
Figure 14B:
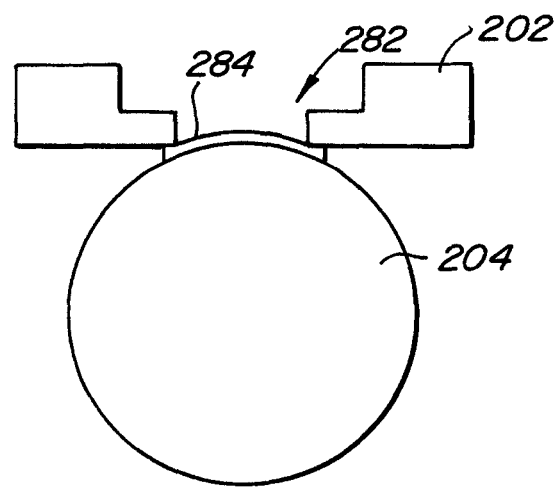
FIG. 14B is an end view of the scraping mechanism of FIG. 14A as mounted above the rotatable member.

Apparatus 200 further includes a mechanism for doctoring any excess powder from metering chambers 242. Such a doctoring mechanism 282 is illustrated in FIGS. 14A and 14B and is also referred to as a doctoring sheet. For convenience of illustration, doctoring mechanism 282 has been omitted from the drawings of FIGS. 10-12. In FIGS. 14A and 14B, rotatable member 204 is shown in schematic view. Doctoring mechanism 282 comprises a thin plate 284 having apertures 286 which are aligned with metering chambers 242 when rotatable member 204 is in the filling position. Apertures 286 preferably have a diameter that is slightly larger than the diameter of metering chambers 242. In this way, apertures 286 will not interfere with the filling of metering chambers 242. Plate 284 is preferably constructed of brass and has a diameter of approximately 0.003 inches. Plate 284 is sprung against rotatable member 204 so that it is generally flush against the outer periphery. In this way, plate 284 is generally sealed against rotatable member 204 to prevent excess powder from escaping between plate 284 and rotatable member 204. Plate 284 is attached to frame 202 and remains stationary while rotatable member 204 rotates. In this way, after powder has been transferred to metering chambers 242, rotatable member 204 is rotated toward the dispensing position. During rotation, the edges of apertures 286 scrape any excess powder from metering chambers 242 so that only a unit dose amount remains in metering chambers 242. Configuration of doctoring mechanism 282 is advantageous in that it reduces the amount of movable parts, thereby reducing the build up of static electricity. Further, the removed powder remains within hopper 206 where it will be available for transfer into metering chambers 242 after they have been emptied.

Figure 14C:
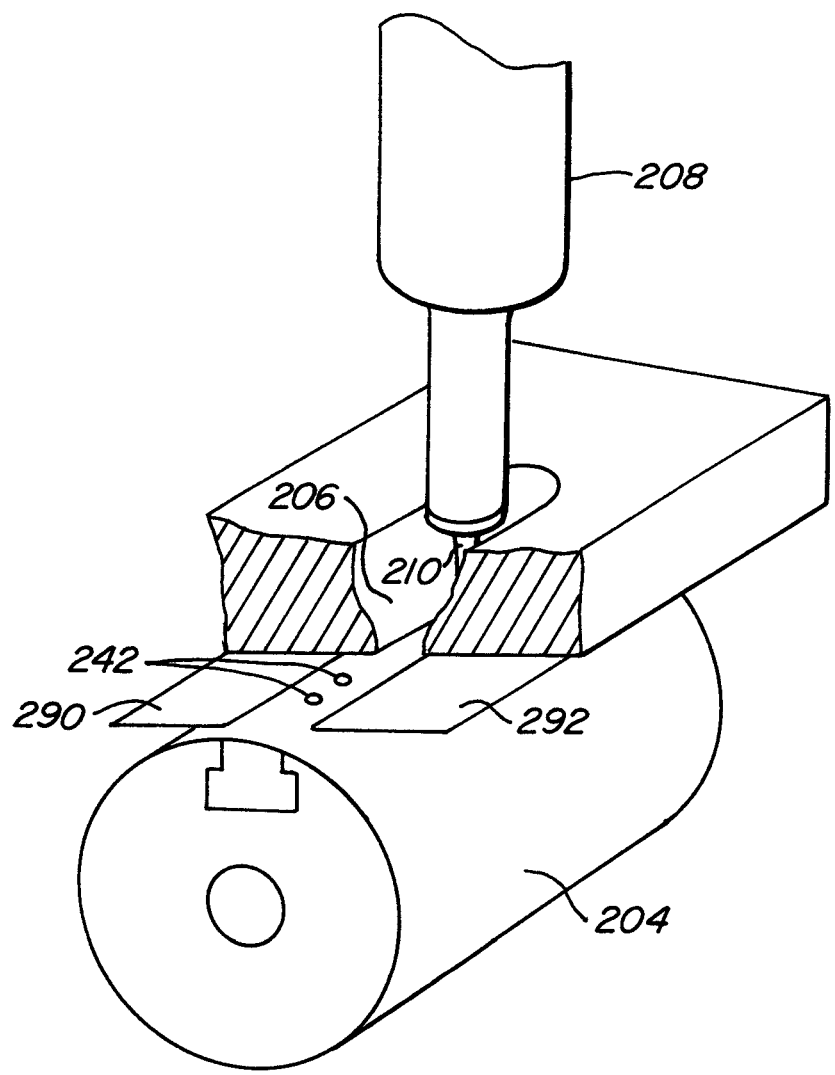
FIG. 14C is a perspective view of an alternative mechanism for scraping excess powder from a chamber of a rotatable member according to the invention.
Figure 15:
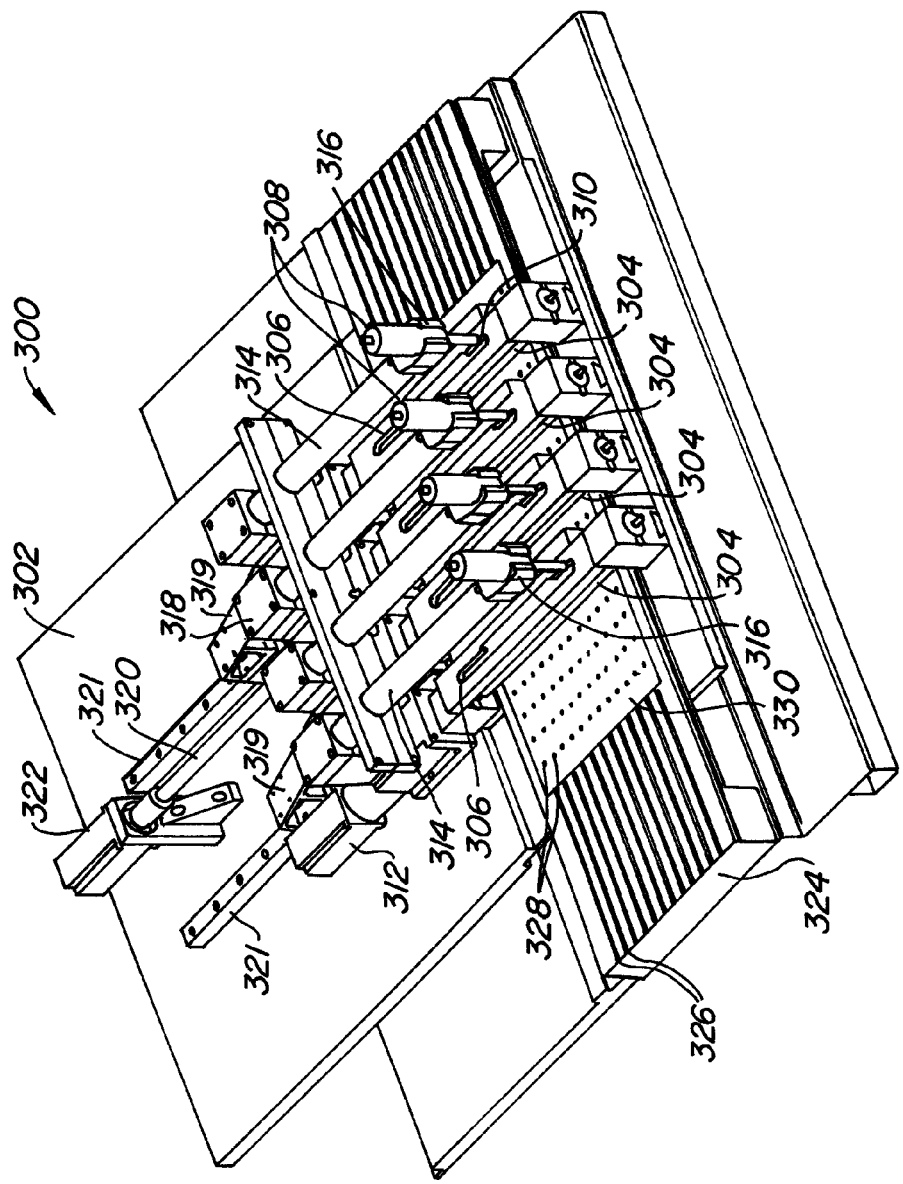
FIG. 15 is a perspective view of a particularly preferable system for transporting powders according to the invention.

Illustrated in FIG. 14C is an alternative mechanism for scraping or doctoring excess powder from metering chambers 242. The mechanism comprises a pair of doctoring blades 290 and 292 which are coupled to hopper 206, it being appreciated that only one blade may be needed depending on the direction of rotation of rotatable member 204. Blades 290 and 292 are preferably constructed of a thin sheet material, such as 0.005 inch brass, and are sprung lightly against rotatable member 204. The edges of blades 290 and 292 coincide approximately with the edges of the opening in hopper 206. After metering chambers 242 are filled, rotatable member 204 is rotated, with blades 290 or 292 (depending on the direction of rotation) scraping any excess powder from metering chambers 242.

Referring back now to FIGS. 10-12, operation of apparatus 200 to fill receptacles with unit dosages of fine powder will be described. Initially, the fine powder is placed into tubular section 224 of secondary hopper 218. Conveniently, hopper 218 may be removed from frame 202 during filling. Housing 222 is then shaken or vibrated for a time sufficient to transfer a desired amount of powder through opening 228, through screen 230 and down chute 226 where it falls into primary hopper 206. Rotatable member 204 is placed in the filling position where metering chambers 242 are aligned with hopper 206. A vacuum is then applied to air inlets 260 and 261 (see FIG. 13) to draw air through metering chambers 242. Under the influence of gravity, and with the assistance of the vacuum, the powder tumbles into the metering chambers 242 and generally fills metering chambers 242. Vibrator 208 is then actuated to vibrate element 210. At the same time, motor 217 is operated to translate vibratable element 210 back and forth within chamber 206. As element 210 is vibrated, end member 240 creates a pattern of air flow at the bottom of hopper 206 to agitate the powder. As end member 240 passes over each metering chamber 242, an aerosol cloud is produced that is drawn into the metering chamber 242 by vacuum and by gravity. As end member 240 passes over metering chambers 242, ultrasonic energy radiates down into metering chambers 242 to agitate the powder already inside the metering chamber. This in turn allows flow within the cavity to even out any irregularities in density that may exist during previous filling. Such a feature is particularly advantageous in that agglomerates or chunks of powder which may create voids in the metering chamber may be broken down to more evenly fill the metering chamber.

After passing one or more times over each of the metering chambers 242, rotatable member 204 is rotated 180° to a dispensing position where metering chambers 242 are aligned with receptacles (not shown). As rotatable member 204 rotates, any excess powder is scraped from metering chambers 242 as previously described. When in the dispensing position, a compressed gas is supplied through air inlets 260 and 261 to expel unit dosages of powder from metering chambers 242 and into the receptacles.

The invention also provides a way to adjust fill weights by modulating the ultrasonic power supplied to vibrator 210 as it passes over metering chambers 242. In this way, fill weights for the various metering chambers may be adjusted to compensate for powder weight discrepancies that may periodically occur. As one example, if the fourth metering chamber was consistently producing a dosage amount that was too low in weight, the power to vibrator 208 could be increased slightly each time it passed over the fourth metering chamber. In conjunction with an automated (or manual) weighing system and a controller, such an arrangement may be used to make an automated (or manual) closed-loop weight control system to adjust the power level of the vibrator for each of the metering chambers to provide more accurate fill weights.

Referring now to FIG. 15, an exemplary embodiment of a system 300 for metering and transporting a fine powder will be described. System 300 operates in a manner similar to apparatus 200 but includes multiple vibrators and multiple hoppers for simultaneously filling a plurality of receptacles with unit dosages of fine powder. System 300 comprises a frame 302 to which are rotatably coupled a plurality of rotatable members 304. Rotatable members 304 may be constructed similar to rotatable member 204 and include a plurality of metering chambers (not shown) for receiving powder. The number of rotatable members and metering chambers may be varied according to the particular application. Disposed above each rotatable member 304 is a primary hopper 306 which holds the powder above rotatable members 304. A vibrator 308 is disposed above each hopper 306 and includes a vibratable element 310 to agitate the powder within hopper 306 in a manner similar to that described in connection with apparatus 200. Although not shown for convenience of illustration, a secondary hopper which is similar to secondary hopper 218 of apparatus 200 will be disposed above each of primary hoppers 306 to transfer powder into hoppers 306 in a manner similar to that described in connection with apparatus 200.

A motor 312 (only one being shown for convenience of illustration) is coupled to each of rotatable members 304 to rotate rotatable members 304 between a filling position and a dispensing position similar to apparatus 200.

Each vibrator 308 is coupled to an arm 314 by a clamp 316. Arms 314 are in turn coupled to a common stage 318 which having slides 319 which are translatable over tracks 321 by a screw 320 of a screw motor 322. In this way, the vibratable elements 310 may simultaneously be moved back and forth in hoppers 306 by operation of screw motor 322. Alternatively, each of vibrators could be coupled to a separate motor so that each vibrator may independently be translated.

Frame 302 is coupled to a base 324 which includes a plurality of elongate grooves 326. Grooves 326 are adapted to receive bottom ends of a plurality of receptacles 328 which are formed in a sheet 330. Sheet 330 is preferably supplied from a blister maker, such as a commercially available Uhlmann Packaging Machine, Model No. 1040. Rotatable members 304 preferably include a number of metering chambers that correspond to the number of receptacles in each row of sheets 330. In this way, four rows of receptacles may be filled during each cycle of operation. Once four of the rows are filled, the metering chambers are again refilled and sheet 330 is advanced to align four new rows of receptacles with hoppers 306.

One particular advantage of system 300 is that it may be fully automated. For example, a controller may be coupled to the packaging machine, vacuum and pressurized gas sources, motors 312, motor 322 and vibrators 308. By use of such a controller, sheet 330 may automatically be advanced to the proper position whereupon motors 312 are actuated to align the metering chambers with hoppers 306. A vacuum source is then actuated to draw a vacuum through the metering chambers while vibrators 308 are actuated and motor 322 is employed to translate vibrators 308. Once the metering chambers are filled, the controller is employed to actuate motors 312 to rotate rotatable members 304 until they are aligned with receptacles 328. The controller then sends a signal to send a pressurized gas through the metering chambers to expel the metered powder into receptacles 328. Once filled, the controller causes the packaging machine to advance the sheet 330 and to repeat the cycle. When needed, the controller may be employed to actuate motors (not shown) to vibrate the secondary hoppers to transfer powder into primary hoppers 306 as previously described.

Although shown with vibrators which comprise ultrasonic horns, it will be appreciated that other types of vibrators and vibratable elements may be employed, including those previously described herein. Further, it will be appreciated that the number of vibrators and size of the troughs may be varied according to the particular need.

Although the foregoing invention has been described in some detail by way of illustration and example, for purposes of clarity of understanding, it will be obvious that certain changes and modifications may be practiced within the scope of the appended claims.

What is claimed is:

1. A receptable containing a unit dose of a fine powder medicament, wherein the receptacle that has been filled by a method comprising:
   placing the fine powder into a hopper having an opening therein;
   vibrating a vibratable element within the fine powder, wherein the vibratable member has a distal end in the vicinity of the opening, and wherein the vibratable member is vibrated in an up and down motion relative to the powder in the hopper;
   moving the distal end of the vibratable element laterally through the fine powder while the vibratable element is vibrating; and
   capturing at least a portion of the fine powder exiting the opening within the receptacle.

2. A receptacle as in claim 1, wherein the vibratable element is coupled to an ultrasonic horn, and wherein the vibrating step comprises actuating the ultrasonic horn.

3. A receptacle as in claim 1, wherein the vibratable element is vibrated at a frequency in the range from about 1,000 Hz to about 180,000 Hz.

4. A receptacle as in claim 1, wherein the distal end has an end-member attached thereto which is vibrated over the opening.

5. A receptacle as in claim 4, wherein the end-member is vertically spaced apart from the opening by a distance in the range from about 0.01 mm to about 10 mm.

6. A receptacle as in claim 1, further comprising moving the distal end of the element across the opening while vibrating the element.

7. A receptacle as in claim 1, wherein the fine powder comprises a medicament composed of individual particles having a mean size in the range from about 1 micrometer to 100 micrometers.

8. A receptacle as in claim 1, wherein the capturing step comprises capturing the powder in a transfer chamber and transferring the powder from the transfer chamber to the receptacle.

9. A receptacle as in claim 8, wherein the capturing step further comprises drawing air through the transfer chamber which is positioned below the opening, wherein the drawn air assists in drawing the fine powder into the transfer chamber.

10. A receptacle as in claim 9, wherein the transferring step comprises introducing a compressed gas into the transfer chamber to expel the captured powder into the receptacle.

* * * * *